United States Patent
Hirata et al.

(10) Patent No.: US 11,191,437 B2
(45) Date of Patent: Dec. 7, 2021

(54) FLUID CONTROL DEVICE

(71) Applicant: Murata Manufacturing Co., Ltd., Kyoto (JP)

(72) Inventors: Atsuhiko Hirata, Kyoto (JP); Kenjiro Okaguchi, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 1115 days.

(21) Appl. No.: 15/412,574

(22) Filed: Jan. 23, 2017

(65) Prior Publication Data
US 2017/0127956 A1 May 11, 2017

Related U.S. Application Data

(63) Continuation of application No. PCT/JP2015/072176, filed on Aug. 5, 2015.

(30) Foreign Application Priority Data

Aug. 11, 2014 (JP) .............................. JP2014-163272

(51) Int. Cl.
*A61B 5/022* (2006.01)
*A61B 5/0235* (2006.01)
(Continued)

(52) U.S. Cl.
CPC ........ *A61B 5/02233* (2013.01); *A61B 5/0235* (2013.01); *F04B 43/0045* (2013.01);
(Continued)

(58) Field of Classification Search
CPC .............. A61B 5/02233; A61B 5/0235; A61B 2560/0214; F04B 49/06; F04B 43/0045;
(Continued)

(56) References Cited

U.S. PATENT DOCUMENTS 4,200,259 A * 4/1980 Ueda .................... A61B 5/0235
251/285
4,479,494 A * 10/1984 McEwen ............ A61B 5/02141
600/495
(Continued)

FOREIGN PATENT DOCUMENTS

JP H05-11905 U 2/1993
JP H06-265044 A 9/1994
(Continued)

OTHER PUBLICATIONS

Electronic Valves, 2019, Clippard, pp. 1-52 (Year: 2019).*
International Search Report issued in Patent Application No. PCT/JP2015/072176 dated Nov. 2, 2015.
Written Opinion issued in Patent Application No. PCT/JP2015/072176 dated Nov. 2, 2015.

*Primary Examiner* — Navin Natnithithadha
(74) *Attorney, Agent, or Firm* — Pearne & Gordon LLP

(57) ABSTRACT

A fluid control device (10) includes a container (13), a pump (11), a solenoid valve (12), and a capacitor. The pump (11) is driven by a main power source, and is capable of pressurizing or depressurizing the inside of the container (13). A suction port and a discharge port of the pump (11) internally communicate with each other. The solenoid valve (12) is connected at both ends thereof to the container (13) and the pump (11). If the voltage of the main power source is reduced or lost, the solenoid valve (12) releases pressure in the container (13) by being driven by the power stored in the capacitor or secondary battery.

13 Claims, 11 Drawing Sheets

(51) Int. Cl.
  *F04B 45/047* (2006.01)
  *F04B 49/06* (2006.01)
  *F16K 31/02* (2006.01)
  *F16K 31/06* (2006.01)
  *F04B 43/00* (2006.01)
  *F04B 43/02* (2006.01)
  *F04B 43/04* (2006.01)
  *F15B 20/00* (2006.01)

(52) U.S. Cl.
  CPC ........ *F04B 43/0081* (2013.01); *F04B 43/026* (2013.01); *F04B 43/046* (2013.01); *F04B 45/047* (2013.01); *F04B 49/06* (2013.01); *F15B 20/00* (2013.01); *F16K 31/02* (2013.01); *F16K 31/06* (2013.01); *A61B 2560/0214* (2013.01)

(58) Field of Classification Search
  CPC .. F04B 43/026; F04B 43/0081; F04B 43/046; F04B 45/047; F15B 20/00; F16K 31/02; F16K 31/06
  USPC ........................................................ 600/499
  See application file for complete search history.

(56) References Cited

U.S. PATENT DOCUMENTS

| | | | | |
|---|---|---|---|---|
| 5,038,820 | A | * | 8/1991 | Ames ...................... F16K 31/02 |
| | | | | 137/460 |
| 5,169,379 | A | * | 12/1992 | Freed .................... A61M 1/106 |
| | | | | 600/17 |
| 6,471,657 | B2 | * | 10/2002 | Sadritabrizi ....... A61B 5/02233 |
| | | | | 600/485 |
| 2007/0283958 | A1 | * | 12/2007 | Naghavi ................. A61F 5/566 |
| | | | | 128/204.18 |
| 2011/0245696 | A1 | * | 10/2011 | Yamashita ........... H02J 7/0025 |
| | | | | 600/493 |
| 2015/0025400 | A1 | | 1/2015 | Nishioka |
| 2015/0150470 | A1 | | 6/2015 | Sano |
| 2015/0154364 | A1 | * | 6/2015 | Biasi ...................... G16H 10/60 |
| | | | | 709/223 |

FOREIGN PATENT DOCUMENTS

JP    2013-220187 A    10/2013
WO    2013/179789 A1    12/2013

* cited by examiner

FLUID CONTROL DEVICE

This is a continuation of International Application No. PCT/JP2015/072176 filed on Aug. 5, 2015 which claims priority from Japanese Patent Application No. 2014-163272 filed on Aug. 11, 2014. The contents of these applications are incorporated herein by reference in their entireties.

FIELD OF THE DISCLOSURE

The present disclosure relates to a fluid control device that controls fluid in a container.

DESCRIPTION OF THE RELATED ART

Examples of conventional fluid control devices include one disclosed in Patent Document 1. This fluid control device includes a cuff having a fluid bag, a pump unit configured to supply air into the fluid bag, a valve configured to open and close for discharging air from or introducing air into the fluid bag, and a CPU configured to control the drive of the pump unit and the valve. The fluid control device controls pressure in the fluid bag by driving the pump unit and the valve.

FIG. 13A is a schematic block diagram of a fluid control device 140 having a conventional configuration. In the fluid control device 140, a container 13 is connected to a pump 11 having a suction port and a discharge port internally communicating with each other. The pump 11 can transfer a fluid by being driven. By stopping the drive of the pump 11, the pump 11 can reverse the flow of the fluid in accordance with a differential pressure between the suction port and the discharge port of the pump 11. Therefore, by repeatedly driving and stopping the pump 11, the fluid control device 140 can control the pressure in the container 13 to a predetermined level. Even if the main power source of the fluid control device 140 is lost, since the fluid in the container 13 is discharged to the outside through the inside of the pump 11, the pressure in the container 13 is released. Thus, even when the fluid control device 140 is used for a human body, the human body can be prevented from being exposed to a hazard by the pressure maintained in the container 13.

FIG. 13B is a schematic block diagram of a fluid control device 150 having a conventional configuration. In the fluid control device 150, a solenoid valve 152 is connected between the pump 11 and the container 13. The solenoid valve 152 has a first port and a second port isolated in the energized state and communicating with each other in the non-energized state. The first port of the solenoid valve 152 is connected to the pump 11, and the second port of the solenoid valve 152 is connected to the container 13. When controlling or releasing pressure in the container 13, the fluid control device 150 opens the solenoid valve 152 by not energizing it. When maintaining the pressure in the container 13, the fluid control device 150 closes the solenoid valve 152 by energizing it. If the main power source of the fluid control device 150 is lost, since the solenoid valve 152 is opened, the pressure in the container 13 is released through the pump 11 and the solenoid valve 152.

FIG. 13C is a schematic block diagram of a fluid control device 160 having a conventional configuration. In the fluid control device 160, the first port of the solenoid valve 152 is connected between a pump 61 and the container 13, and the second port of the solenoid valve 152 is connected to the outside. The pump 61 prevents the backflow of the fluid in the non-energized state. When controlling or maintaining the pressure in the container 13, the fluid control device 160 closes the solenoid valve 152 by energizing it. When releasing the pressure in the container 13 to the outside, the fluid control device 160 opens the solenoid valve 152 by not energizing it. If the main power source of the fluid control device 160 is lost, since the solenoid valve 152 is opened, the pressure in the container 13 is released through the solenoid valve 152.

Patent Document 1: Japanese Unexamined Patent Application Publication No. 2013-220187

BRIEF SUMMARY OF THE DISCLOSURE

Studies done by the present inventors will now be described.

When keeping the pressure in the container 13 constant, the fluid control device 140 needs to continuously drive the pump 11, and this increases the power consumption. Inserting a check valve between the pump 11 and the container 13 makes it possible to keep the pressure in the container 13 constant without driving the pump 11. However, this makes it unable to release the pressure in the container 13.

When keeping the pressure in the container 13 constant, the fluid control device 150 needs to continuously energize the solenoid valve 152 to close it, and this increases the power consumption. When controlling or maintaining the pressure in the container 13, the fluid control device 160 also needs to continuously energize the solenoid valve 152 to close it, and this increases the power consumption.

An object of the present disclosure is to provide a fluid control device that is capable of releasing the pressure in the container when the power is shut off while reducing the power consumption.

A fluid control device according to the present disclosure includes a container, a pump, a valve, and a capacitor or secondary battery. The pump is driven by a main power source, and is capable of pressurizing or depressurizing an inside of the container. A suction port and a discharge port of the pump internally communicate with each other. The valve connects to or communicates with the container and the pump at one or both ends thereof. If a voltage of the main power source is reduced or lost, the valve releases the pressure in the container by being driven by the power stored in the capacitor or secondary battery.

With this configuration, if the voltage of the main power source is reduced or lost, the pressure in the container is released. The container can thus be prevented from remaining pressurized.

The fluid control device according to the present disclosure may be configured in the following manner. The valve has a first port connected to the pump and a second port connected to the container, allows the first port and the second port to communicate with each other in an energized state, and isolates the first port and the second port in a non-energized state. If the voltage of the main power source is reduced or lost, the valve is energized by the power stored in the capacitor or secondary battery.

The fluid control device according to the present disclosure may be configured in the following manner. The valve has a first port connected to an outside and a second port connected to the pump, allows the first port and the second port to communicate with each other in an energized state, and isolates the first port and the second port in a non-energized state. If the voltage of the main power source is reduced or lost, the valve is energized by the power stored in the capacitor or secondary battery.

With the configurations described above, the pressure in the container is maintained by isolating the first port and the second port of the valve. Since the valve is not energized when the pressure in the container is maintained, it is possible to reduce the power consumption. If the voltage of the main power source is reduced or lost, the valve is energized by the power stored in the capacitor or secondary battery. Since this allows the first port and the second port to communicate with each other, the pressure in the container is released.

In the fluid control device according to the present disclosure, the capacitor or secondary battery is preferably supplied with the power from the main power source.

In the fluid control device according to the present disclosure, the pump may pressurize the inside of the container. The fluid control device according to the present disclosure may measure a blood pressure on the basis of the pressure in the container.

With this configuration, the inside of the container is pressurized by driving the pump and isolating the first port and the second port of the valve. Since the valve is not energized when the inside of the container is pressurized, it is possible to reduce the power consumption. Also, since the pressure in the container is released when the main power source is shut off or the voltage of the main power source drops, the safety of a person to be measured can be ensured.

In the fluid control device according to the present disclosure, the container may be a cuff.

The fluid control device according to the present disclosure may be configured in the following manner. The fluid control device according to the present disclosure includes a drive circuit configured to energize the valve. The drive circuit includes the capacitor or secondary battery connected to a direct-current power source via a diode, and a coil for driving the valve. The drive circuit further includes a switch for applying the power stored in the capacitor or secondary battery to the coil if the voltage of the main power source is reduced or lost.

With this configuration, if the main power source is shut off or the voltage of the main power source drops, a voltage is applied to the coil for driving the valve by switching the switch. Since this allows the first port and the second port of the valve to communicate with each other, the pressure in the container is released.

According to the present disclosure, it is possible not only to reduce the power consumption, but also to release the pressure in the container when the power is shut off.

DETAILED DESCRIPTION OF THE DISCLOSURE

First Embodiment

Figure 1A:
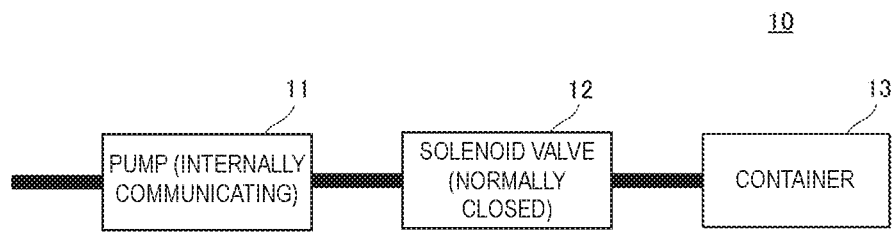
FIG. 1A is a schematic block diagram of a fluid control device according to a first embodiment.

A fluid control device 10 according to a first embodiment of the present disclosure will be described. For example, the fluid control device 10 is used as a pressure massaging device that repeatedly compresses a body with an air bag. FIG. 1A is a schematic block diagram of the fluid control device 10. The fluid control device 10 includes a pump 11, a solenoid valve 12, a container 13, and a drive circuit 14 (see FIG. 3). The solenoid valve 12 corresponds to "valve" of the present disclosure. The pump 11 is connected via a tube to the solenoid valve 12. The solenoid valve 12 is connected via a tube to the container 13. The pump 11 and the solenoid valve 12 are driven by the drive circuit 14. In the fluid control device 10, the pressure in the container 13 is controlled by the operation of the pump 11. The pump 11, the solenoid valve 12, and the container 13 may be directly connected without tubes.

The pump 11 has a structure in which a suction port and a discharge port thereof internally communicate with each other. In the non-energized state, the fluid can be transferred inside the pump 11 in accordance with a differential pressure between the suction port and the discharge port. The pump 11 is driven by a piezoelectric element. The solenoid valve 12 is opened and closed by movement of a plunger caused by magnetic force produced by energizing a coil. The solenoid valve 12 has a first port and a second port communicating with each other in the energized state and isolated (not communicating with each other) in the non-energized state. The container 13 has an inner space for storing the fluid therein, and an opening communicating with the inner space.

The suction port of the pump 11 communicates with the outside via a flow passage in a tube. The discharge port of the pump 11 communicates with the first port of the solenoid valve 12 via a flow passage in the tube. The second port of the solenoid valve 12 communicates with the opening of the container 13 via a flow passage in the tube. That is, the pump 11 is connected to the container 13 to pressurize the inside of the container 13.

Figure 1B:
FIG. 1B is a schematic block diagram of a fluid control device according to a modification of the first embodiment.

FIG. 1B is a schematic block diagram of a fluid control device according to a modification of the first embodiment. The solenoid valve 12 is connected via a tube to the pump 11. The pump 11 is connected via a tube to the container 13. The first port of the solenoid valve 12 communicates with the outside via a flow passage in a tube. The second port of the solenoid valve 12 communicates with the suction port of the pump 11 via a flow passage in the tube. The discharge port of the pump 11 communicates with the opening of the container 13 via a flow passage in the tube. This fluid control device operates in the same manner as the fluid control device 10.

Figure 2A:
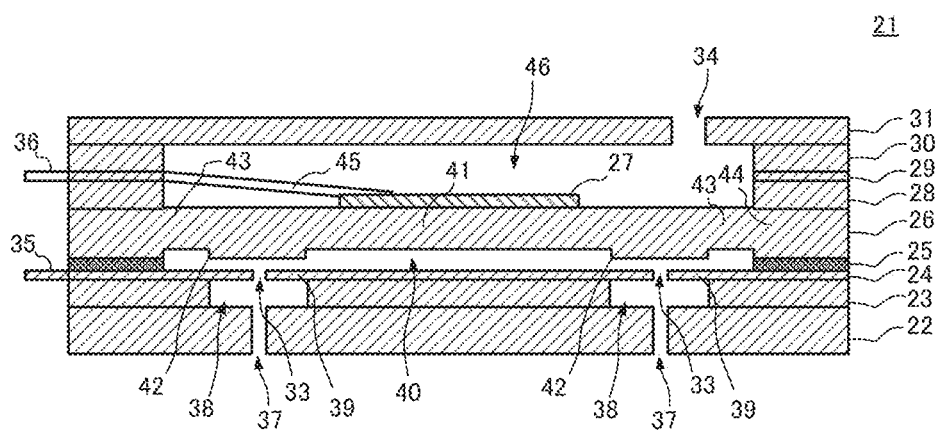
FIG. 2A is a schematic cross-sectional view of a piezoelectric pump according to the first embodiment.

FIG. 2A is a schematic cross-sectional view of a piezoelectric pump 21. The piezoelectric pump 21 is an example of the pump 11. The piezoelectric pump 21 is constructed by stacking a cover plate 22, a flow passage plate 23, a counter plate 24, an adhesive layer 25, a vibrating plate 26, a piezoelectric element 27, an insulating plate 28, a feeding plate 29, a spacer plate 30, and a lid plate 31 in this order. The piezoelectric pump 21 is thin in the stacking direction and rectangular in plan view (as viewed from the stacking direction). The piezoelectric pump 21 has suction ports 33 on the side of the cover plate 22. The piezoelectric pump 21 has a discharge port 34 on the side of the lid plate 31. The discharge port 34 of the piezoelectric pump 21 is connected via a tube to the first port of the solenoid valve 12 as described above.

The cover plate 22 has circular flow passage holes 37. The flow passage plate 23 has circular cavities 38. The cavities 38 communicate with the respective flow passage holes 37. The cavities 38 are greater in diameter than the flow passage holes 37. The counter plate 24 is made of metal. The counter plate 24 has an external connection terminal 35 protruding outward, and the suction ports 33 circular in shape. The suction ports 33 communicate with the respective cavities 38. The suction ports 33 are smaller in diameter than the cavities 38. Thus, bendable movable portions 39 are formed around the respective suction ports 33 in the counter plate 24.

The adhesive layer 25 is formed in the shape of a frame to coincide with a frame portion 44 of the vibrating plate 26. The adhesive layer 25 is made of a thermosetting resin, such as an epoxy resin, containing a plurality of conductive particles with a substantially uniform diameter. This makes it possible to achieve a uniform thickness of the adhesive layer 25 over the entire circumference by making the thickness substantially the same as the diameter of the conductive particles. Also, the counter plate 24 and the vibrating plate 26 can be electrically connected, with the conductive particles of the adhesive layer 25 interposed therebetween.

The vibrating plate 26 is made of metal, such as SUS301. The vibrating plate 26 faces the counter plate 24 at a given distance therefrom. The space between the counter plate 24 and the vibrating plate 26 forms a pump chamber 40. The vibrating plate 26 has a center portion 41, striking portions 42, connecting portions 43, and the frame portion 44. The center portion 41 is circular in plan view, and is positioned in the center of the vibrating plate 26. The frame portion 44 has a frame shape in plan view, and is positioned in the outer region of the vibrating plate 26. The connecting portions 43 have a beam-like shape and connect the center portion 41 to the frame portion 44. The striking portions 42 are circular in plan view and are each positioned around the boundary between the center portion 41 and the corresponding connecting portion 43. The striking portions 42 are each positioned to face the corresponding suction port 33 in the center thereof. The striking portions 42 are greater in diameter than the suction ports 33. The striking portions 42 and the frame portion 44 are thicker than the center portion 41 and the connecting portions 43. The vibrating plate 26 has a cavity (not shown) surrounded by the components thereof described above. The pump chamber 40 communicates with the pump chamber 46, with the cavity interposed therebetween.

The piezoelectric element 27 is formed by placing electrodes on both principal surfaces of a thin plate made of a piezoelectric material. The piezoelectric element 27 has piezoelectricity that allows the piezoelectric element 27 to expand or contract in area in the in-plane direction by being subjected to an electric field in the thickness direction. The piezoelectric element 27 has a disk shape and is affixed to the upper surface of the center portion 41 of the vibrating plate 26. The electrode on the lower surface of the piezoelectric element 27 is electrically connected to the external connection terminal 35 via the vibrating plate 26, the adhesive layer 25, and the counter plate 24.

The insulating plate 28 is made of an insulating resin. The insulating plate 28 has a cavity which is rectangular in plan view. The feeding plate 29 is made of metal. The feeding plate 29 has a cavity which is rectangular in plan view, an internal connection terminal 45 protruding toward the cavity of the feeding plate 29, and an external connection terminal 36 protruding outward. An end portion of the internal connection terminal 45 is soldered to the electrode on the upper surface of the piezoelectric element 27. The spacer plate 30 is made of resin. The spacer plate 30 has a cavity which is rectangular in plan view. The cavities of the insulating plate 28, feeding plate 29, and spacer plate 30 communicate with one another to form the pump chamber 46. The lid plate 31 has the discharge port 34 which is circular in plan view. The discharge port 34 communicates with the pump chamber 46 and the outside.

Figure 2B:
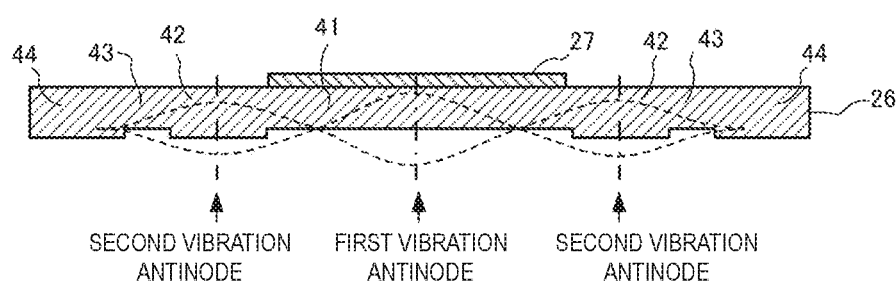
FIG. 2B is a schematic diagram illustrating an operation of the piezoelectric pump according to the first embodiment.

FIG. 2B is a schematic diagram illustrating an operation of the piezoelectric pump 21. In the piezoelectric pump 21, when an alternating drive voltage is applied to the external connection terminals 35 and 36, the piezoelectric element 27 tries to isotropically expand and contract in the in-plane direction. This produces concentric bending vibration of a multilayer body composed of the piezoelectric element 27 and the vibrating plate 26 in the thickness direction. This bending vibration is in higher-order resonant mode. The frame portion 44 serves as a fixed portion, the center of the center portion 41 corresponds to a first vibration antinode, and the center of each striking portion 42 corresponds to a second vibration antinode.

Vibration of the striking portions 42 is transmitted to the movable portions 39 via fluid facing the striking portions 42. The vibration of the striking portions 42 and the vibration of the movable portions 39 are coupled to each other, and cause the fluid in the pump chamber 40 to flow from the vicinity of the suction ports 33 toward the outer side of the movable portions 39. Thus, in the pump chamber 40, a negative pressure is produced around the suction ports 33, from which the fluid is suctioned into the pump chamber 46. Additionally, a positive pressure is produced inside the pump chamber 46 and released from the discharge port 34 in the lid plate 31. Thus, the fluid suctioned via the suction ports 33 into the pump chambers 40 and 46 flows out of the pump chambers 40 and 46 via the discharge port 34.

Figure 3:
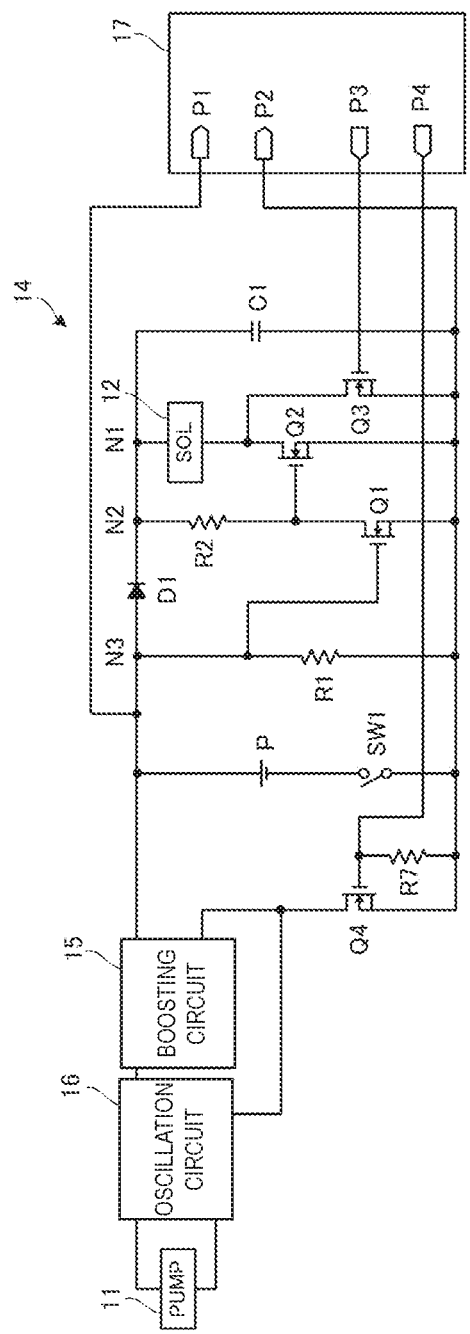
FIG. 3 is a circuit configuration diagram of a drive circuit according to the first embodiment.

FIG. 3 is a circuit configuration diagram of the drive circuit 14. The drive circuit 14 includes a capacitor C1, a diode D1, transistors Q1 to Q4, resistors R1, R2, and R7, a switch SW1, a boosting circuit 15, an oscillation circuit 16, and a microcontroller 17. The capacitor C1 is, for example, an electric double layer capacitor. A secondary battery may be used instead of the capacitor C1. Examples of the secondary battery include a lithium-ion battery and a nickel-metal-hydride battery. The transistors Q1 to Q4 are, for example, MOSFETs. The transistor Q2 corresponds to "switch" of the present disclosure. The drive circuit 14 is connected to a main power source P. The main power source P is a direct-current power source, such as a battery. The drive circuit 14 and the main power source P are connected and disconnected by a switch SW1. Instead of using a direct-current power source as the main power source, the output of an alternating-current power source may be converted by an AC/DC converter.

The capacitor C1 is connected between the main power source P and the ground. The diode D1 is connected between the main power source P and the capacitor C1. The anode of the diode D1 is connected to the main power source P, and the cathode of the diode D1 is connected to the capacitor C1. A node N1 between the diode D1 and the capacitor C1 is connected via the solenoid valve 12 to the drains of the transistor Q2 and transistor Q3. The sources of the transistor Q2 and transistor Q3 are connected to the ground. A node N2 between the diode D1 and the node N1 is connected via the resistor R2 to the drain of the transistor Q1. The source of the transistor Q1 is connected to the ground. A node between the resistor R2 and the transistor Q1 is connected to the gate of the transistor Q2. A node N3 between the main power source P and the diode D1 is connected via the resistor R1 to the ground, and is also connected to the gate of the transistor Q1.

The boosting circuit 15 is connected to the main power source P, and is also connected to the drain of the transistor Q4. The oscillation circuit 16 is connected to the pump 11 and the boosting circuit 15, and is also connected to the drain of the transistor Q4. The source of the transistor Q4 is connected to the ground. The microcontroller 17 includes terminals P1 to P4. The terminal P1 is a power terminal connected to the main power source P. The terminal P2 is a ground terminal connected to the ground. The terminal P3 is connected to the gate of the transistor Q3. The terminal P4 is connected to the gate of the transistor Q4. The microcontroller 17 outputs a solenoid valve drive signal from the terminal P3, and outputs a pump drive signal from the terminal P4. A node between the gate of the transistor Q4 and the terminal P4 is connected via the resistor R7 to the ground.

When the fluid control device 10 is used, the switch SW1 is turned on. This turns on the main power source P in the drive circuit 14, and causes the electric charge to be stored in the capacitor C1. That is, the power is stored in the capacitor C1 while the main power source P is on.

When the pressure in the container 13 is controlled by the operation of the pump 11, the switch SW1 is on, the solenoid valve drive signal goes high, and the pump drive signal is output in a predetermined waveform. When the pump drive signal goes high, the transistor Q4 turns on and a voltage from the main power source P is applied to the boosting circuit 15. The boosting circuit 15 boosts the voltage from the main power source P and outputs it. Since the transistor Q4 turns on, the voltage output from the boosting circuit 15 is supplied to the oscillation circuit 16. The oscillation circuit generates a drive voltage for driving the pump 11. The pump 11 is driven by the drive voltage. When the pump drive signal goes low, the transistor Q4 turns off. Accordingly, no drive voltage is applied to the pump 11 and the pump 11 is stopped. The output of the pump 11 is controlled by repeatedly driving and stopping the pump 11 in accordance with the pump drive signal. Since the solenoid valve drive signal goes high, the transistor Q3 turns on. Thus, since the solenoid valve 12 is energized by the main power source P, the solenoid valve 12 is opened to allow the pump 11 to communicate with the inside of the container 13. The pressure in the container 13 is thus controlled in accordance with the operation of the pump 11.

When the pressure in the container 13 is maintained, the switch SW1 is on and the solenoid valve drive signal and the pump drive signal go low. Since the switch SW1 is on, the transistor Q1 turns on and the transistor Q2 turns off. Since the solenoid valve drive signal goes low, the transistor Q3 turns off. Thus, since the solenoid valve 12 is not energized, the solenoid valve 12 is closed to isolate the pump 11 and the inside of the container 13. This makes it possible to maintain the pressure in the container 13. When the pump drive signal goes low, the transistor Q4 turns off. The pump 11 is thus stopped since no drive voltage is applied thereto.

When the use of the fluid control device 10 is terminated or the main power source P is lost for some reasons, the main power source P is isolated from the drive circuit 14 (or the main power source P is shut off). Shutting off the main power source P corresponds to turning off the switch SW1. On the other hand, the power stored in the capacitor C1 while the main power source P is on is supplied to the drive circuit 14. Since a voltage from the capacitor C1 is not applied to the gate of the transistor Q1 because of the rectifying action of the diode D1, the transistor Q1 turns off and the transistor Q2 turns on. Thus, since the solenoid valve 12 is energized by the power stored in the capacitor C1, the solenoid valve 12 is opened to allow the pump 11 to communicate with the inside of the container 13. As described above, the suction port and the discharge port of the pump 11 internally communicate with each other. This allows the inside of the container 13 to communicate with the outside of the fluid control device 10. Also, since the power stored in the capacitor C1 is not supplied to the pump 11 and the microcontroller 17 because of the rectifying action of the diode D1, the pump 11 is not driven. Therefore, in accordance with a differential pressure between the inside of the container 13 and the outside of the fluid control device 10, the fluid in the container 13 is discharged to the outside and the pressure in the container 13 is released to the outside. When the amount of electric charge stored in the capacitor C1 becomes insufficient, the solenoid valve 12 cannot be easily energized and is closed. That is, during several seconds after the main power source P is shut off and before the amount of electric charge stored in the capacitor C1 becomes insufficient, the pressure in the container 13 is released to the outside.

In the first embodiment, when the pressure in the container 13 is maintained, since the solenoid valve 12 is not energized, the power is not consumed by the solenoid valve 12 and is consumed only by the resistors in the drive circuit 14. Therefore, the power consumption during the use of the fluid control device 10 can be reduced. When the main power source P is shut down, since the solenoid valve 12 is opened for several seconds by the power stored in the capacitor C1, the pressure in the container 13 can be released to the outside.

Using an electric double layer capacitor as the capacitor C1, or using a secondary battery instead of the capacitor C1, makes it possible to store a larger amount of power. Thus, when the main power source P is shut down, since the solenoid valve 12 is opened for a certain length of time, it is possible to reliably release the pressure in the container 13.

Second Embodiment

Figure 4:
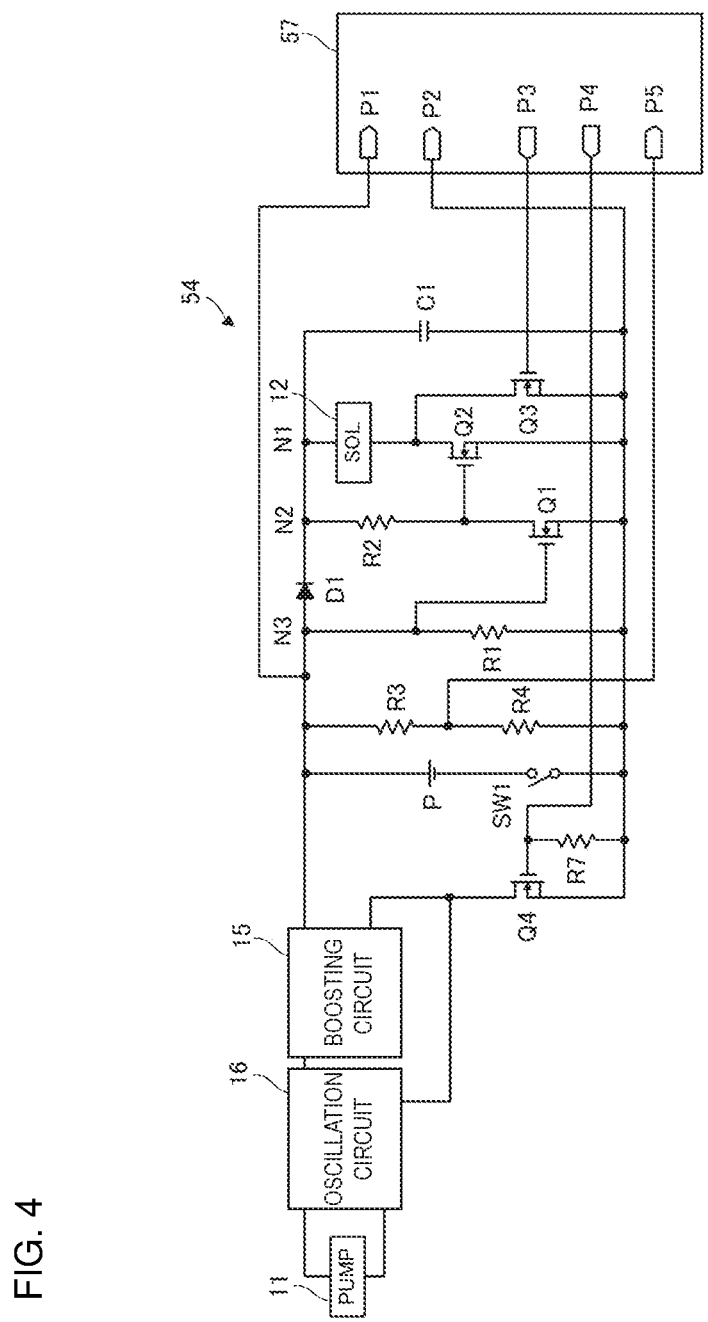
FIG. 4 is a circuit configuration diagram of a drive circuit according to a second embodiment.

A fluid control device according to a second embodiment of the present disclosure will be described. The fluid control device of the second embodiment is configured in the same manner as the fluid control device 10 of the first embodiment (see FIG. 1A), except for a drive circuit 54 of the second embodiment. FIG. 4 is a circuit configuration diagram of the drive circuit 54. A node between the main power source P and the node N3 is connected to the ground via resistors R3 and R4 connected in series. A node between the resistor R3 and the resistor R4 is connected to a terminal P5 of a microcontroller 57. The terminal P5 is an input terminal of an A/D converter. The other configuration of the drive circuit 54 is the same as that of the drive circuit 14.

The voltage of the main power source P divided by the resistors R3 and R4 is applied to the terminal P5 of the microcontroller 57. The microcontroller 57 converts the voltage applied to the terminal P5 into a digital value. If the digital value is greater than a threshold, the microcontroller 57 determines that the voltage of the main power source P is within a normal range, whereas if the digital value is smaller than the threshold, the microcontroller 57 determines that the voltage of the main power source P has dropped. A voltage drop in the main power source P is thus detected. The threshold is set such that normal operation of the fluid control device is secured at around or above the threshold.

If a voltage drop in the main power source P is detected, the solenoid valve drive signal goes high and the pump drive signal goes low. Since the pump drive signal goes low, the pump 11 is stopped. Since the solenoid valve drive signal goes high, the solenoid valve 12 is opened to allow the inside of the container 13 to communicate with the outside of the fluid control device. Thus, the fluid in the container 13 is discharged to the outside, and the pressure in the container 13 is released to the outside. The pump drive signal is not output until the voltage of the main power source P returns to a normal value. That is, the operation of the pump 11 is prohibited until the fluid control device is restarted after battery replacement or the like. Note that the operations that the fluid control device performs when pressure is controlled, the pressure is maintained, and the power is shut off are the same as those in the first embodiment.

When the voltage of the main power source P drops, the fluid control device may not operate properly. For example, due to a voltage drop in the main power source P, the transistor Q2 may not properly turn on and off, and thus, the solenoid valve 12 may not be opened and closed. In the second embodiment, if a voltage drop in the main power source P is detected, the solenoid valve 12 is opened and the fluid in the container 13 is discharged to the outside. Therefore, even when the voltage of the main power source P gradually decreases, the pressure in the container 13 can be released to the outside. Also, since the pump 11 is not driven until the fluid control device is restarted, it is possible to prevent a malfunction of the fluid control device. The same effect as that of the first embodiment can also be achieved.

Third Embodiment

Figure 5:
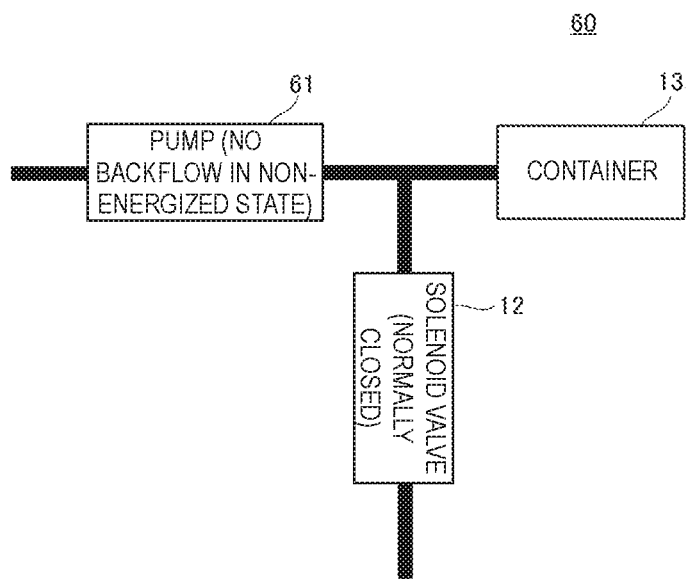
FIG. 5 is a schematic block diagram of a fluid control device according to a third embodiment.

A fluid control device 60 according to a third embodiment of the present disclosure will be described. FIG. 5 is a schematic block diagram of the fluid control device 60. The fluid control device 60 includes the pump 61, the solenoid valve 12, the container 13, and a drive circuit 64 (see FIG. 7). The suction port of the pump 61 communicates with the outside via a flow passage in a tube. The discharge port of the pump 61 communicates with the opening of the container 13 via a flow passage in a tube. The first port of the solenoid valve 12 communicates with the flow passage in the tube positioned between the pump 61 and the container 13. The second port of the solenoid valve 12 communicates with the outside via a flow passage in a tube. That is, the pump 61 is connected to the container 13 to pressurize the inside of the container 13. The pump 61 prevents the backflow of the fluid in the non-energized state. That is, when the pump 61 is not energized, no fluid flows through the inside of the pump 61 from the discharge port to the suction port of the pump 61. The pump 61 is driven by a direct-current motor.

Figure 6:
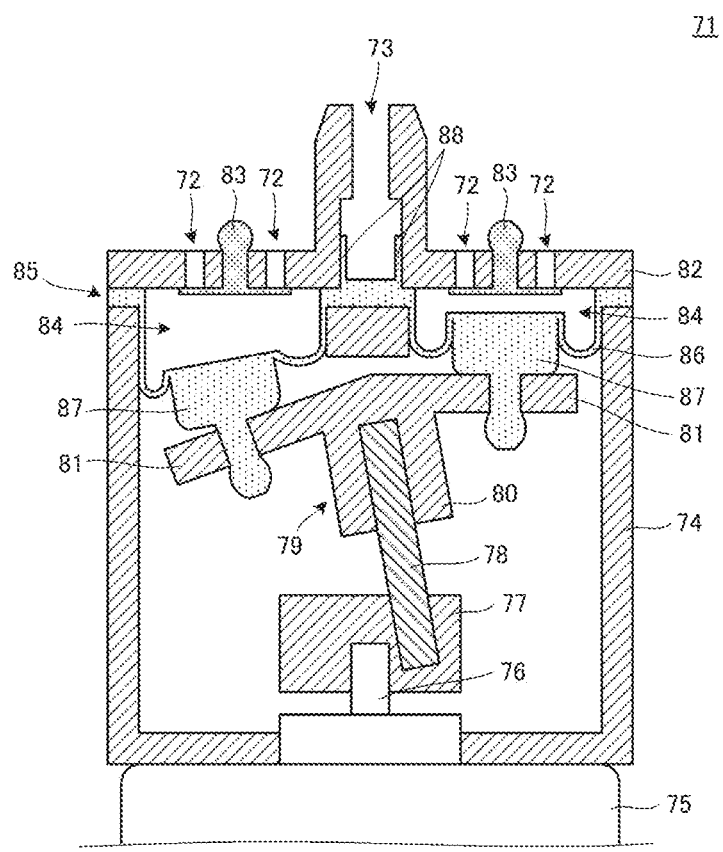
FIG. 6 is a schematic cross-sectional view of a diaphragm pump according to the third embodiment.

FIG. 6 is a schematic cross-sectional view of a diaphragm pump 71. The diaphragm pump 71 is an example of the pump 61. The diaphragm pump 71 has suction ports 72 and a discharge port 73. The discharge port 73 of the diaphragm pump 71 is connected, via the tube, to the first port of the solenoid valve 12 and the opening of the container 13 as described above.

A case 74 has a substantially cylindrical shape with a bottom. A motor 75 driven by a direct-current voltage is attached to the bottom of the case 74. An output shaft 76 of the motor 75 is inserted into the case 74 from an opening in the bottom of the case 74. A crank base 77 is secured to the output shaft 76. A drive shaft 78 is mounted at an angle to the crank base 77. A drive body 79 is mounted on the drive shaft 78. The drive body 79 is composed of a bearing 80 and a pair of drive units 81. The drive shaft 78 is rotatably inserted into the bearing 80. The pair of drive units 81 protrudes in opposite directions from the bearing 80. A lid 82 is attached to the upper part of the case 74. The lid 82 has the suction ports 72 and the discharge port 73. The suction ports 72 in the lid 82 are provided with suction valves 83. The suction valves 83 are formed of an elastic material. The suction valves 83 allow flow only from the suction ports 72 to pump chambers 84.

The pump chambers 84 are defined by a diaphragm 85 which partitions off part of the inner space of the case 74. The diaphragm 85 is formed of an elastic material. The diaphragm 85 has a diaphragm portion 86, piston portions 87, and discharge valves 88. The diaphragm portion 86 is formed in the shape of a thin film. The piston portions 87 extend downward from the diaphragm portion 86 and are attached to the respective drive units 81. The discharge valves 88 extend from the diaphragm portion 86 along the inner wall of the discharge port 73. The discharge valves 88 allow the flow only from the pump chambers 84 to the discharge port 73.

When the motor 75 is driven by a drive voltage, the output shaft 76 and the crank base 77 rotate to periodically change the direction of the inclination of the drive shaft 78. As the direction of the inclination of the drive shaft 78 changes, the inclination of the drive units 81 of the drive body 79 periodically changes, the piston portions 87 reciprocate, and the volume of the pump chambers 84 periodically changes. When the volume of the pump chambers 84 increases, the pump chambers 84 are depressurized, the discharge valves 88 are closed, the suction valves 83 are opened, and the fluid is suctioned from the suction ports 72 into the pump chambers 84. When the volume of the pump chambers 84 decreases, the pump chambers 84 are pressurized, the suction valves 83 are closed, the discharge valves 88 are opened, and the fluid is discharged from the pump chambers 84 to the discharge port 73. Thus, the fluid suctioned from the suction ports 72 is discharged from the discharge port 73. Since the suction valves 83 and the discharge valves 88 of the diaphragm pump 71 are check valves, no backflow occurs even in the non-energized state.

Figure 7:
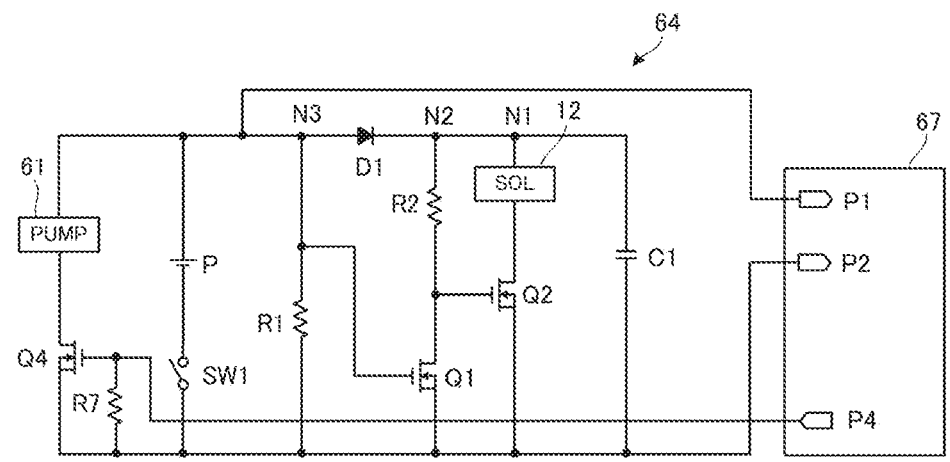
FIG. 7 is a circuit configuration diagram of a drive circuit according to the third embodiment.

FIG. 7 is a circuit configuration diagram of the drive circuit 64. The drain of the transistor Q4 is directly connected to the pump 61. The drive circuit 64 does not include the transistor Q3 of the first embodiment. A microcontroller 67 does not include the terminal P3 of the first embodiment. The other configuration of the drive circuit 64 is the same as that of the drive circuit 14.

When the pressure in the container 13 is controlled by the operation of the pump 61, the switch SW1 is on and the pump drive signal is outputted in a predetermined waveform. When the pump drive signal goes high, the transistor Q4 turns on. Accordingly, a direct-current drive voltage is applied to the pump 61 and the pump 61 is driven. When the pump drive signal goes low, the transistor Q4 turns off. Accordingly, no drive voltage is applied to the pump 61 and the pump 61 is stopped. The output of the pump 61 is controlled by repeatedly driving and stopping the pump 61 in accordance with the pump drive signal. Since the switch SW1 is on, the transistor Q1 turns on and the transistor Q2 turns off. Thus, since the solenoid valve 12 is not energized, the solenoid valve 12 is closed. The pressure in the container 13 is thus controlled in accordance with the operation of the pump 61.

When the pressure in the container 13 is maintained, the switch SW1 is on and the pump drive signal goes low. Since the switch SW1 is on, the solenoid valve 12 is closed as is the case with above. Also, since the pump drive signal goes low, the transistor Q4 turns off and the pump 61 is not energized. Therefore, as described above, the fluid does not flow backward in the pump 61. Since the inside of the container 13 and the outside of the fluid control device 60 are thus isolated, the pressure in the container 13 is maintained. Since the pump 61 is not energized, the pump 61 is not driven.

When the main power source P is isolated from the drive circuit 64, the solenoid valve 12 is opened for several seconds and the pump 61 is stopped as in the case of the first embodiment. Therefore, the fluid in the container 13 is discharged through the solenoid valve 12 to the outside in accordance with a differential pressure between the inside of the container 13 and the outside of the fluid control device 60. As a result, the pressure in the container 13 is released to the outside.

In the third embodiment, the same effect as that of the first embodiment can be achieved by using the pump 61 having a structure which does not cause backflow in the non-energized state. Since a direct-current motor is used to drive the pump 61, the pump 61 can be driven by a low direct-current voltage. Therefore, the drive circuit 64 does not require a boosting circuit or an oscillation circuit. This simplifies the configuration of the drive circuit 64. Also, the solenoid valve 12 does not need to be controlled by the microcontroller 67.

Fourth Embodiment

Figure 8:
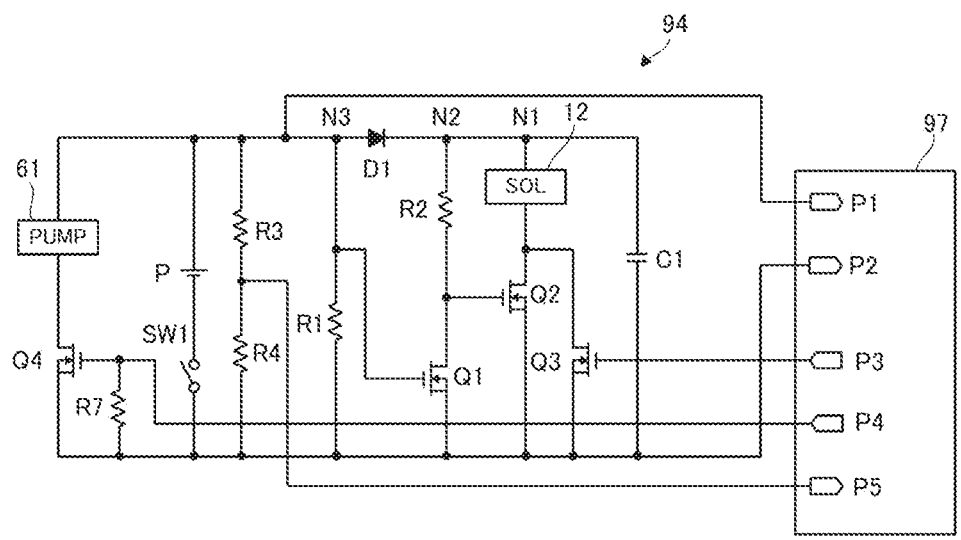
FIG. 8 is a circuit configuration diagram of a drive circuit according to a fourth embodiment.

A fluid control device according to a fourth embodiment of the present disclosure will be described. The fluid control device of the fourth embodiment is configured in the same manner as the fluid control device 60 of the third embodiment (see FIG. 5), except for a drive circuit 94 of the fourth embodiment. FIG. 8 is a circuit configuration diagram of the drive circuit 94. The node between the main power source P and the node N3 is connected to the ground via the resistors R3 and R4 connected in series. The node between the resistor R3 and the resistor R4 is connected to the terminal P5 of a microcontroller 97. The terminal P5 is an input terminal of an A/D converter. A node between the solenoid valve 12 and the drain of the transistor Q2 is connected to the drain of the transistor Q3. The source of the transistor Q3 is connected to the ground. The gate of the transistor Q3 is connected to the terminal P3 of the microcontroller 97. The microcontroller 97 outputs a solenoid valve drive signal from the terminal P3. The other configuration of the drive circuit 94 is the same as that of the drive circuit 64.

When pressure in the container 13 is controlled by the operation of the pump 61, the switch SW1 is on, the solenoid valve drive signal goes low, and the pump drive signal is outputted in a predetermined waveform. The pump 61 operates in accordance with the pump drive signal. Since the switch SW1 is on, the transistor Q1 turns on and the transistor Q2 turns off. Since the solenoid valve drive signal goes low, the transistor Q3 also turns off. Thus, since the solenoid valve 12 is not energized, the solenoid valve 12 is closed. Pressure in the container 13 is thus controlled in accordance with the operation of the pump 61.

When pressure in the container 13 is maintained, the switch SW1 is on, and the solenoid valve drive signal and the pump drive signal go low. Since the switch SW1 is on and the solenoid valve drive signal goes low, the solenoid valve 12 is closed as is the case with above. Also, since the pump drive signal goes low, the pump 61 is not energized. Therefore, the fluid does not flow backward in the pump 61. Since the inside of the container 13 and the outside of the fluid control device are thus isolated, the pressure in the container 13 is maintained.

As in the second embodiment, the microcontroller 97 detects a voltage drop in the main power source P on the basis of a voltage applied to the terminal P5. When a voltage drop in the main power source P is detected, the solenoid valve drive signal goes high and the pump drive signal goes low. Since the pump drive signal goes low, the pump 61 is stopped. Since the solenoid valve drive signal goes high, the solenoid valve 12 is opened to allow the inside of the container 13 to communicate with the outside of the fluid control device. Thus, the fluid in the container 13 is discharged to the outside, and pressure in the container 13 is released to the outside. The pump drive signal is not output until the voltage of the main power source P returns to a normal value. That is, the operation of the pump 61 is prohibited until the fluid control device is restarted after battery replacement or the like. Note that the operation that the fluid control device performs when the power is shut off is the same as that in the third embodiment.

In the fourth embodiment, the same effect as that of the second embodiment can be achieved by using the pump 61 having a structure which does not cause backflow in the non-energized state.

Fifth Embodiment

Figure 9:
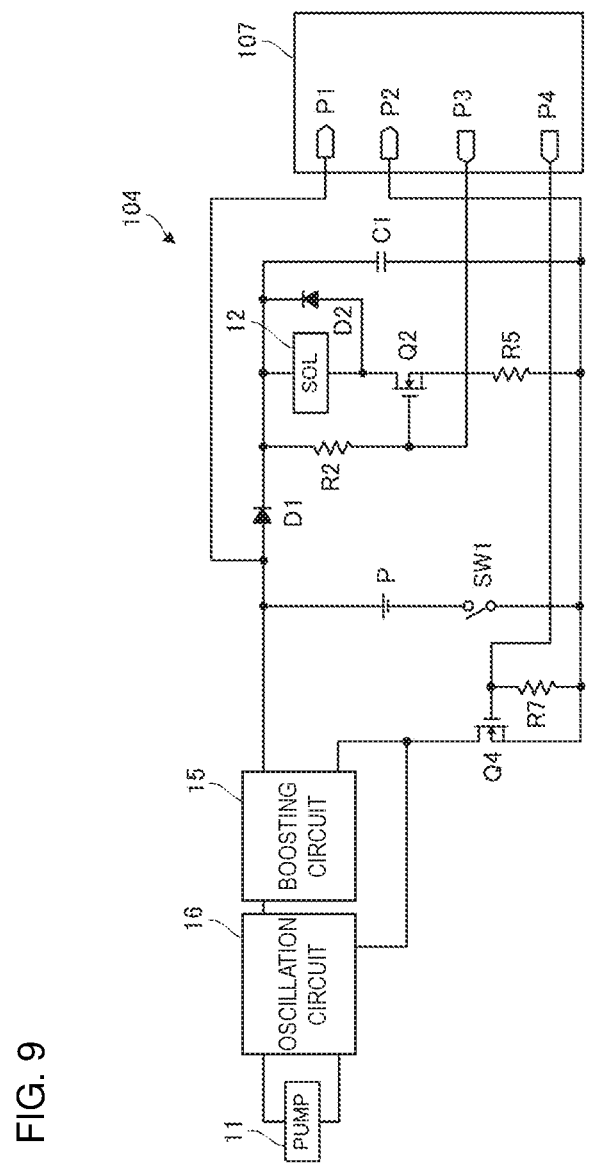
FIG. 9 is a circuit configuration diagram of a drive circuit according to a fifth embodiment.

A fluid control device according to a fifth embodiment of the present disclosure will be described. The fluid control device of the fifth embodiment is configured in the same manner as the fluid control device 10 of the first embodiment (see FIG. 1A), except for a drive circuit 104 of the fifth embodiment. FIG. 9 is a circuit configuration diagram of the drive circuit 104. A node between the resistor R2 and the gate of the transistor Q2 is connected to the terminal P3 of the microcontroller 107. The microcontroller 107 outputs a solenoid valve drive signal from the terminal P3. The source of the transistor Q2 is connected via the resistor R5 to the ground. The diode D2 is connected in parallel to the solenoid valve 12. The transistors Q1 and Q3 and the resistor R1 of the first embodiment (see FIG. 3) are not provided. The other configuration of the drive circuit 104 is the same as that of the drive circuit 14. The diode D1 may not be provided if the drive circuit is configured not to allow an electric charge stored in the capacitor C1 to flow to the pump 11 and the microcontroller 107. The diode D2 is provided to protect the solenoid valve 12 from overvoltage.

When the pressure in the container 13 is controlled by the operation of the pump 11, the switch SW1 is on, the solenoid valve drive signal goes high, and the pump drive signal is outputted in a predetermined waveform. The pump 11 operates in accordance with the pump drive signal. Since the solenoid valve drive signal goes high, the transistor Q2 turns on, and the solenoid valve 12 is energized by the main power source P and opened. The pressure in the container 13 is thus controlled in accordance with the operation of the pump 11.

When the pressure in the container 13 is maintained, the switch SW1 is on, and the solenoid valve drive signal and the pump drive signal go low. Since the solenoid valve drive signal goes low, the transistor Q2 turns off. Therefore, since the solenoid valve 12 is not energized and is closed, the pressure in the container 13 is maintained. Also, since the pump drive signal goes low, the transistor Q4 turns off and the pump 11 is stopped.

When the main power source P is isolated from the drive circuit 104, the terminal P3 of the microcontroller 107 is brought into a high impedance state. The power stored in the capacitor C1 while the main power source P is on is supplied to the drive circuit 104. Therefore, the transistor Q2 turns on and the solenoid valve 12 is energized. As a result, during several seconds after the main power source P is shut off and before the amount of electric charge stored in the capacitor C1 becomes insufficient, the solenoid valve 12 is opened and the pressure in the container 13 is released to the outside. As described above, the pump 11 is not driven because the power stored in the capacitor C1 is not supplied to the pump 11 and the microcontroller 107.

When the voltage of the main power source P drops, the terminal P3 of the microcontroller 107 is also brought into a high impedance state. Thus, the transistor Q2 turns on, and the solenoid valve 12 is energized and opened. Therefore, the fluid in the container 13 is discharged to the outside and the pressure in the container 13 is released to the outside. When the voltage of the main power source P drops, the terminal P4 of the microcontroller 107 is also brought into a high impedance state. Thus, since the transistor Q4 turns off, the pump 11 is not driven.

In the fifth embodiment, the circuit configuration of the drive circuit 104 is simplified by using the fact that if the main power source P is shut off or the voltage of the main power source P drops, an input and output terminal of the microcontroller is brought into a high impedance state. Specifically, the number of transistors included in the drive circuit 104 is reduced to one, and the need for a circuit configuration for detecting a voltage drop in the main power source P is eliminated. That is, in the fifth embodiment, it is possible to achieve the same effect as that of the embodiments described above while simplifying the circuit configuration of the drive circuit 104.

Sixth Embodiment

Figure 10:
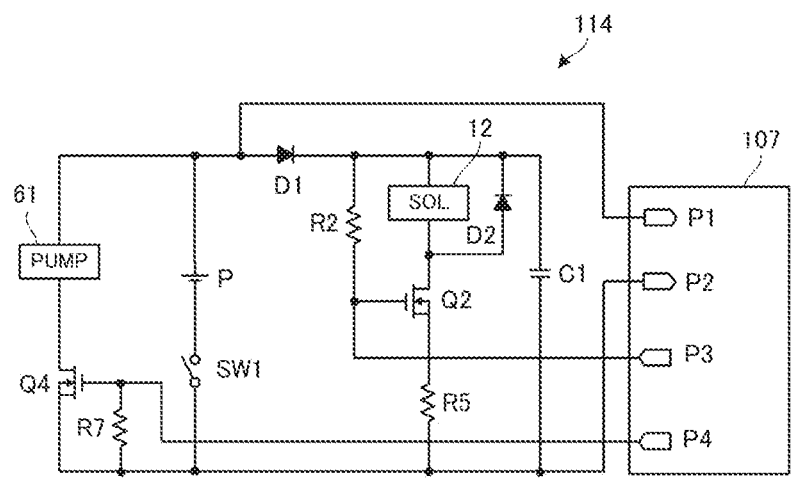
FIG. 10 is a circuit configuration diagram of a drive circuit according to a sixth embodiment.

A fluid control device according to a sixth embodiment of the present disclosure will be described. The fluid control device of the sixth embodiment is configured in the same manner as the fluid control device 60 of the third embodiment (see FIG. 5), except for a drive circuit 114 of the sixth embodiment. FIG. 10 is a circuit configuration diagram of the drive circuit 114. The drive circuit 114 is configured in the same manner as the drive circuit 104 of the fifth embodiment (see FIG. 9), except that the drain of the transistor Q4 is directly connected to the pump 61.

When the pressure in the container 13 is controlled by the operation of the pump 61, the switch SW1 is on, the solenoid valve drive signal goes low, and the pump drive signal is outputted in a predetermined waveform. The pump 61 operates in accordance with the pump drive signal. Since the solenoid valve drive signal goes low, the transistor Q2 turns off and the solenoid valve 12 is not energized and is closed. The pressure in the container 13 is thus controlled in accordance with the operation of the pump 61.

When the pressure in the container 13 is maintained, the switch SW1 is on, and the solenoid valve drive signal and the pump drive signal go low. Since the solenoid valve drive signal goes low, the transistor Q2 turns off. Therefore, the solenoid valve 12 is not energized and is closed. Also, since the pump drive signal goes low, the transistor Q4 turns off and the pump 61 is not energized. Therefore, as described above, the fluid does not flow backward in the pump 61. Since the inside of the container 13 and the outside of the fluid control device are thus isolated, the pressure in the container 13 is maintained.

When the main power source P is isolated from the drive circuit 114 or the voltage of the main power source P drops, the solenoid valve 12 is opened and the pressure in the container 13 is released to the outside, as in the case of the fifth embodiment. The pump 61 is not driven as in the case of the fifth embodiment.

In the sixth embodiment, the same effect as that of the fifth embodiment can be achieved by using the pump 61 having a structure which does not cause the backflow in the non-energized state.

Seventh Embodiment

Figure 11:
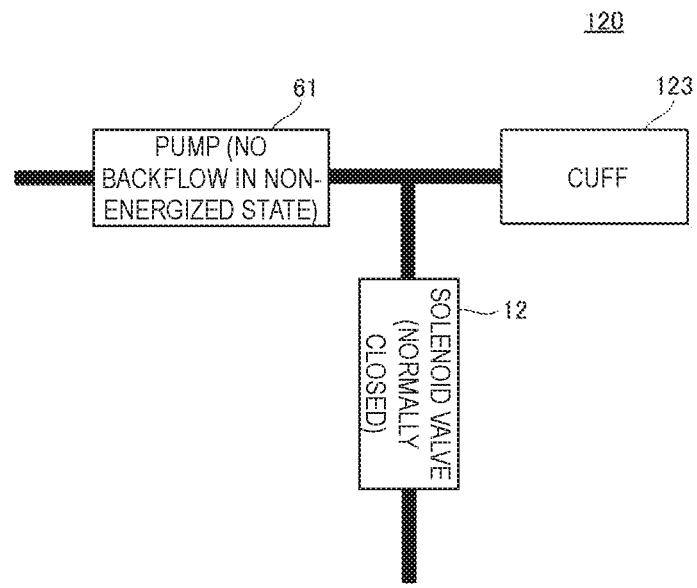
FIG. 11 is a schematic block diagram of a fluid control device according to a seventh embodiment.

A fluid control device 120 according to a seventh embodiment of the present disclosure will be described. The fluid control device 120 is used as a sphygmomanometer. FIG. 11 is a schematic block diagram of the fluid control device 120. The fluid control device 120 has a configuration similar to that of the fluid control device of the sixth embodiment, and includes a cuff 123 as the container 13 of the sixth embodiment. The fluid control device 120 also has a configuration (not shown), such as a pressure sensor, required for the measurement of blood pressure.

When measuring blood pressure, the user turns on the main power source of the fluid control device 120 and performs a predetermined operation. By the same operation as that in the sixth embodiment, the fluid control device 120 closes the solenoid valve 12 and drives the pump 61 to pressurize the inside of the cuff 123. The fluid control device 120 measures blood pressure by detecting a pulse wave with the pressure sensor while pressurizing the inside of the cuff 123. That is, the fluid control device 120 measures blood pressure on the basis of the pressure in the cuff 123.

Upon completion of the measurement of blood pressure, the pump drive signal goes low, the transistor Q4 (see FIG. 10) turns off, and the pump 61 is stopped. The solenoid valve drive signal goes high, the transistor Q2 turns on, and the solenoid valve 12 is energized by the main power source P and opened. The solenoid valve 12 is opened for several seconds, and this allows air in the cuff 123 to be discharged to the outside.

When the main power source P is isolated from the drive circuit 114 or the voltage of the main power source P drops, the solenoid valve 12 is opened as in the case of the fifth embodiment, and air in the cuff 123 is discharged to the outside. The pump 61 is not driven as in the case of the fifth embodiment.

Figure 13A:
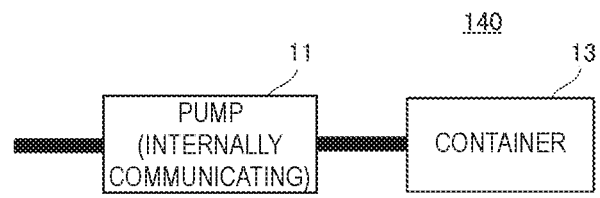
FIG. 13A is a schematic block diagram of a fluid control device 140 having a conventional configuration.
Figure 13B:
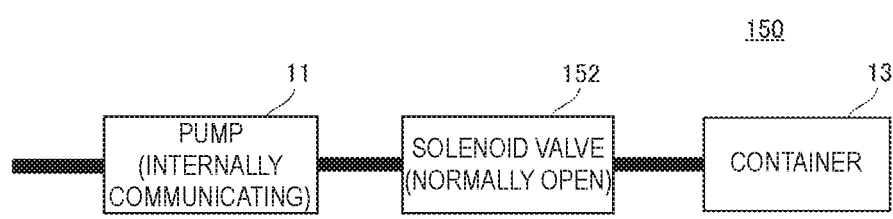
FIG. 13B is a schematic block diagram of a fluid control device 150 having a conventional configuration.
Figure 13C:
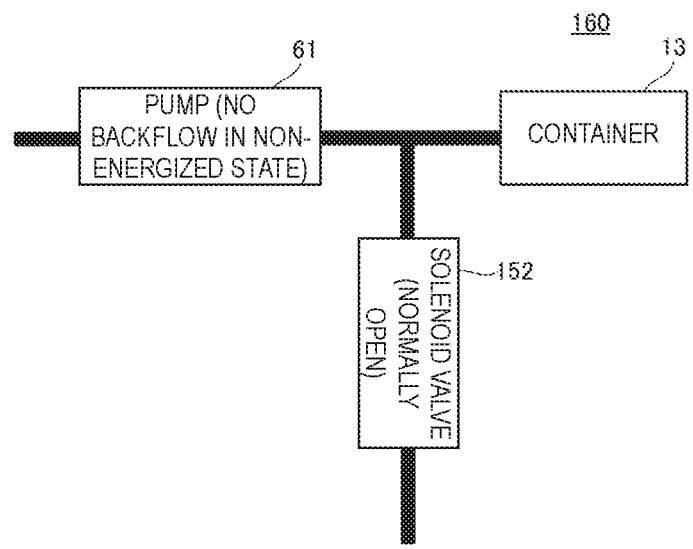
FIG. 13C is a schematic block diagram of a fluid control device 160 having a conventional configuration.
Figure 14:
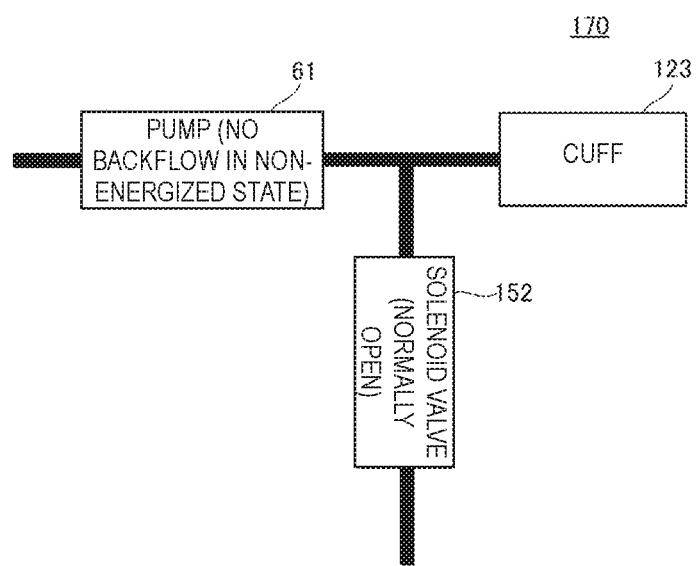
FIG. 14 is a schematic block diagram of a fluid control device 170 having a conventional configuration.

FIG. 14 is a schematic block diagram of a fluid control device 170 having a conventional configuration. The fluid control device 170 is used as a sphygmomanometer. The fluid control device 170 has a configuration similar to the conventional configuration of the fluid control device 160 (see FIG. 13C), and includes the cuff 123 as the container 13 of the fluid control device 160. The fluid control device 170 also has a configuration (not shown), such as a pressure sensor, required for measurement of blood pressure.

When measuring blood pressure, the fluid control device 170 energizes the solenoid valve 152 to close it, and drives the pump 61 to pressurize the cuff 123 at a predetermined rate. The fluid control device 170 measures blood pressure by detecting a pulse wave with the pressure sensor while pressurizing the inside of the cuff 123. To end the measurement of blood pressure, the fluid control device 170 stops the pump 61 and opens the solenoid valve 152 by not energizing it, thereby allowing air inside the cuff 123 to be discharged to the outside.

In the fluid control device 170, the solenoid valve 152 is opened when not being energized. Therefore, in the fluid control device 170, the solenoid valve 152 is opened when the main power source is shut off. Thus, when the power is shut off, a person to be measured can be prevented from being exposed to a hazard by the unreleased pressure in the cuff 123. However, in the fluid control device 170, the solenoid valve 152 needs to be continuously energized during the measurement of blood pressure so that the solenoid valve 152 is closed.

On the other hand, in the fluid control device 120, when the power is shut off, the solenoid valve 12 is opened for several seconds to release the pressure in the cuff 123. This makes it possible to ensure safety. Also, in the fluid control device 120, since the solenoid valve 12 is closed in the non-energized state, the solenoid valve 12 does not need to be energized for the measurement of blood pressure. That is, the fluid control device 120 consumes less power than the fluid control device 170 having a conventional configuration, and can ensure safety.

Eighth Embodiment

Figure 12:
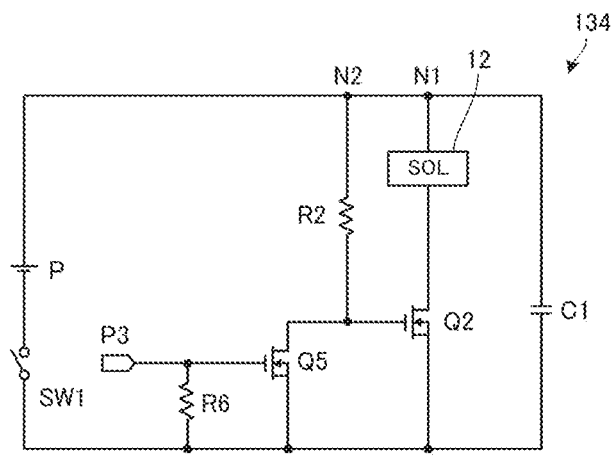
FIG. 12 is a circuit configuration diagram of a drive circuit according to an eighth embodiment.

A fluid control device according to an eighth embodiment of the present disclosure will be described. The fluid control device of the eighth embodiment is configured in the same manner as the fluid control device 10 of the first embodiment (see FIG. 1A), except for a drive circuit 134 of the eighth embodiment. FIG. 12 is a circuit configuration diagram of the drive circuit 134. The drive circuit of the pump 11 and the microcontroller are not shown in FIG. 12.

The capacitor C1 is connected between the main power source P and the ground. The node N1 between the main power source P and the capacitor C1 is connected via the solenoid valve 12 to the drain of the transistor Q2. The source of the transistor Q2 is connected to the ground. The node N2 between the main power source P and the node N1 is connected via the resistor R2 to the gate of the transistor Q2 and also to the drain of the transistor Q5. The source of the transistor Q5 is connected to the ground. The gate of the transistor Q5 is connected to the terminal P3 of the microcontroller. The microcontroller outputs a solenoid valve drive signal from the terminal P3. A node between the gate of the transistor Q5 and the terminal P3 of the microcontroller is connected via a resistor R6 to the ground. A diode may be inserted between the main power source P and the node N2.

When the pressure in the container 13 is controlled by the operation of the pump 11, the switch SW1 is on and the solenoid valve drive signal goes low. Thus, the transistor Q5 turns off and the transistor Q2 turns on. Therefore, the solenoid valve 12 is energized by the main power source P and is opened. The pressure in the container 13 is thus controlled in accordance with the operation of the pump 11.

When the pressure in the container 13 is maintained, the switch SW1 is on and the solenoid valve drive signal goes high. Thus, the transistor Q5 turns on and the transistor Q2 turns off. Therefore, since the solenoid valve 12 is not energized and is closed, the pressure in the container 13 is maintained. The pump 11 is not driven at this point.

If the main power source P is shut off or the voltage of the main power source P drops, the solenoid valve drive signal goes low because a supply voltage to the microcontroller also drops. Thus, the transistor Q5 turns off and the transistor Q2 turns on. Therefore, since the solenoid valve 12 is energized and opened, the pressure in the container 13 is released to the outside. The pump 11 is not driven at this point.

In the eighth embodiment, if the main power source P is shut off or the voltage of the main power source P drops, the pressure in the container 13 can be released to the outside regardless of the impedance state of the terminal P3 of the microcontroller. Also, when the pressure in the container 13 is maintained, the power consumption can be reduced.

Ninth Embodiment

A fluid control device according to a ninth embodiment of the present disclosure will be described. The fluid control device of the ninth embodiment is configured in the same manner as the fluid control device 60 of the third embodiment (see FIG. 5), except for a drive circuit. The drive circuit of the ninth embodiment is configured in the same manner as the drive circuit 134 of the eighth embodiment (see FIG. 12).

When the pressure in the container 13 is controlled by the operation of the pump 61, the switch SW1 is on and the solenoid valve drive signal goes high. Accordingly, the transistor Q5 turns on and the transistor Q2 turns off. Therefore, the solenoid valve 12 is not energized and is closed. The pressure in the container 13 is thus controlled in accordance with the operation of the pump 61.

When the pressure in the container 13 is maintained, the switch SW1 is on and the solenoid valve drive signal goes high. Thus, as is the case with above, the solenoid valve 12 is not energized and is closed. Since the pump 61 is not energized, the fluid does not flow backward in the pump 61. Since the inside of the container 13 and the outside of the fluid control device are thus isolated, the pressure in the container 13 is maintained.

If the main power source P is shut off or the voltage of the main power source P drops, the solenoid valve 12 is opened and the pressure in the container 13 is released to the outside, as in the case of the eighth embodiment. In this case, the pump 61 is not driven, as in the case of the eighth embodiment.

In the ninth embodiment, the same effect as that of the eighth embodiment can be achieved by using the pump 61 having a structure which does not cause backflow in the non-energized state.

Although the inside of the container is pressurized from the outside of the fluid control device in the embodiments described above, the inside of the container may be depressurized from the outside of the fluid control device. In this case, the suction port of the pump is connected to the container side, and the discharge port of the pump is connected to the outside.

Although the pump 11 is driven by a piezoelectric element in the embodiments described above, the present disclosure is not limited to this. The present disclosure is applicable as long as a pump having a structure which allows a suction port and a discharge port to internally communicate with each other is appropriately positioned with other components.

Although the pump 61 is driven by a direct-current motor in the embodiments described above, the present disclosure is not limited to this. The present disclosure is applicable as long as a pump that prevents the backflow of the fluid in the non-energized state is appropriately positioned with other components. For example, instead of the pump 61, the pump 11 having a check valve attached to the suction port or discharge port thereof may be used.

Although the output of the pump is controlled by repeatedly driving and stopping the pump in the embodiments described above, the present disclosure is not limited to this. In the present invention, the output of the pump may be controlled by varying the magnitude of the drive voltage of the pump.

C1: capacitor
D1, D2: diode
N1 to N3: node
P: main power source
P1 to P5: terminal
Q1, Q3 to Q5: transistor
Q2: transistor (switch)
R1 to R7: resistor
SW1: switch
10, 60, 120, 140, 150, 160, 170: fluid control device
11, 61: pump
12, 152: solenoid valve (valve)
13: container
14, 54, 64, 94, 104, 114, 134: drive circuit
15: boosting circuit
16: oscillation circuit
17, 57, 67, 97, 107: microcontroller
21: piezoelectric pump
22: cover plate
23: flow passage plate
24: counter plate
25: adhesive layer
26: vibrating plate
27: piezoelectric element
28: insulating plate
29: feeding plate
30: spacer plate
31: lid plate
33: suction port
34: discharge port
35, 36: external connection terminal
37: flow passage hole
38: cavity
39: movable portion
40, 46: pump chamber
41: center portion
42: striking portion
43: connecting portion
44: frame portion
45: internal connection terminal
71: diaphragm pump
72: suction port
73: discharge port
74: case
75: motor
76: output shaft
77: crank base
78: drive shaft
79: drive body
80: bearing
81: drive unit
82: lid
83: suction valve
84: pump chamber
85: diaphragm
86: diaphragm portion
87: piston portion
88: discharge valve
123: cuff

The invention claimed is:

1. A fluid control device comprising:
a container;
a pump driven by a main power source, configured to be capable of pressurizing or depressurizing an inside of the container, and having a suction port and a discharge port internally communicating with each other;
a valve connected to or communicating with the container and the pump at one or both ends of the valve; and
a capacitor or secondary battery,
wherein upon a voltage of the main power source being reduced or lost, the valve automatically releases a pressure in the container by being driven by power stored in the capacitor or secondary battery, and
wherein operation of the pump restarts only after power is provided to the pump at a level of that of the main power source prior to voltage having been reduced or lost.

2. The fluid control device according to claim 1, wherein the valve has a first port connected to the pump and a second port connected to the container, allows the first port and the second port to communicate with each other in an energized state, isolates the first port and the second port in a non-energized state, and is energized by the power stored in the capacitor or secondary battery if the voltage of the main power source is reduced or lost.

3. The fluid control device according to claim 1, wherein the valve has a first port connected to an outside and a second port connected to the pump, allows the first port and the second port to communicate with each other in an energized state, isolates the first port and the second port in a non-energized state, and is energized by the power stored in the capacitor or secondary battery if the voltage of the main power source is reduced or lost.

4. The fluid control device according to claim 1, wherein the capacitor or secondary battery is supplied with power from the main power source.

5. The fluid control device according to claim 1, wherein the pump pressurizes the inside of the container; and
the fluid control device measures a blood pressure based on the pressure in the container.

6. The fluid control device according to claim 1, wherein the container is a cuff.

7. The fluid control device according to claim 1, further comprising a drive circuit configured to energize the valve, wherein the drive circuit includes the capacitor or secondary battery connected to a direct-current power source via a diode, a coil for driving the valve, and a switch for applying the power stored in the capacitor or secondary battery to the coil if the voltage of the main power source is reduced or lost.

8. The fluid control device according to claim 2, further comprising a drive circuit configured to energize the valve, wherein the drive circuit includes the capacitor or secondary battery connected to a direct-current power source via a diode, a coil for driving the valve, and a switch for applying the power stored in the capacitor or secondary battery to the coil if the voltage of the main power source is reduced or lost.

9. The fluid control device according to claim 3, further comprising a drive circuit configured to energize the valve, wherein the drive circuit includes the capacitor or secondary battery connected to a direct-current power source via a diode, a coil for driving the valve, and a switch for applying the power stored in the capacitor or secondary battery to the coil if the voltage of the main power source is reduced or lost.

10. The fluid control device according to claim 4, further comprising a drive circuit configured to energize the valve, wherein the drive circuit includes the capacitor or secondary battery connected to a direct-current power source via a diode, a coil for driving the valve, and a switch for applying the power stored in the capacitor or secondary battery to the coil if the voltage of the main power source is reduced or lost.

11. The fluid control device according to claim 5, further comprising a drive circuit configured to energize the valve, wherein the drive circuit includes the capacitor or secondary battery connected to a direct-current power source via a diode, a coil for driving the valve, and a switch for applying the power stored in the capacitor or secondary battery to the coil if the voltage of the main power source is reduced or lost.

12. The fluid control device according to claim 6, further comprising a drive circuit configured to energize the valve, wherein the drive circuit includes the capacitor or secondary battery connected to a direct-current power source via a diode, a coil for driving the valve, and a switch for applying the power stored in the capacitor or secondary battery to the coil if the voltage of the main power source is reduced or lost.

13. The fluid control device according to claim 1, wherein a pump drive signal is output only after the main power source outputs voltage at a normal value equal to or greater than prior to voltage reduction or loss, or after a supplemental main power source provides said voltage.

* * * * *